(12) United States Patent
Okita

(10) Patent No.: US 11,259,690 B2
(45) Date of Patent: Mar. 1, 2022

(54) VARIABLE STIFFNESS APPARATUS

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 286 days.

(21) Appl. No.: 16/421,566

(22) Filed: May 24, 2019

(65) Prior Publication Data

US 2019/0313885 A1 Oct. 17, 2019

Related U.S. Application Data

(63) Continuation of application No. PCT/JP2016/085199, filed on Nov. 28, 2016.

(51) Int. Cl.
*A61B 1/005* (2006.01)
*A61B 1/00* (2006.01)
*A61M 25/00* (2006.01)

(52) U.S. Cl.
CPC .......... *A61B 1/0055* (2013.01); *A61B 1/0058* (2013.01); *A61B 1/00006* (2013.01); *A61M 25/0053* (2013.01)

(58) Field of Classification Search
CPC .... A61B 1/0055; A61B 1/0058; A61B 1/0078
See application file for complete search history.

(56) References Cited

U.S. PATENT DOCUMENTS

| 5,055,101 A | * | 10/1991 | McCoy | A61M 25/09 604/528 |
| 2017/0321666 A1 | * | 11/2017 | Morishima | A61B 1/0055 |
| 2018/0266402 A1 | * | 9/2018 | Takahashi | F16F 1/021 |

FOREIGN PATENT DOCUMENTS

| JP | S58-101601 U | 7/1983 |
| JP | H5-91971 A | 4/1993 |
| JP | H05-168586 A | 7/1993 |
| JP | 2005-046273 A | 2/2005 |
| WO | WO 2016/174741 A1 | 11/2016 |

OTHER PUBLICATIONS

International Search Report dated Jan. 10, 2017 issued in PCT/JP2016/085199.

(Continued)

*Primary Examiner* — Aaron B Fairchild
(74) *Attorney, Agent, or Firm* — Scully, Scott, Murphy & Presser, P.C.

(57) ABSTRACT

A variable stiffness apparatus to be installed in a flexible member includes a first elongated member, a second elongated member arranged along the first elongated member, and an inducing member. The first elongated member includes a high bending stiffness portion, and a low bending stiffness portion. The second elongated member includes a shape-memory member that takes a low-stiffness state when in a first phase and a high-stiffness state when in a second phase. The inducing member causes a region of the shape memory member that is arranged around the low bending stiffness portion to transition in phase between the first phase and the second phase, so as to change the stiffness of the region of the second elongated member.

15 Claims, 17 Drawing Sheets

(56) References Cited

OTHER PUBLICATIONS

Japanese Office Action dated Oct. 29, 2019 in Japanese Patent Application No. 2018-552372.
English translation of International Preliminary Report on Patentability dated Jun. 6, 2019, together with the Written Opinion received in related International Application No. PCT/JP2016/085199.

* cited by examiner

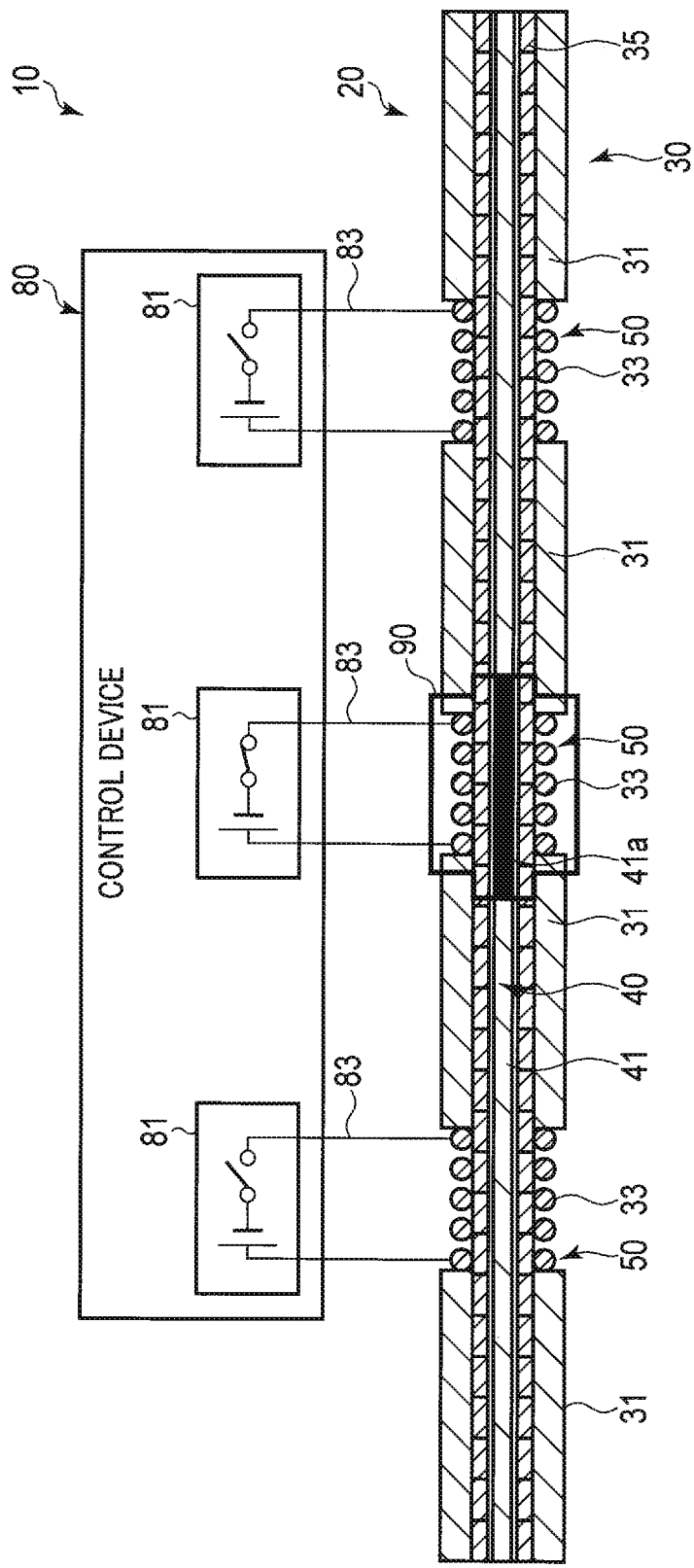
F I G. 1B

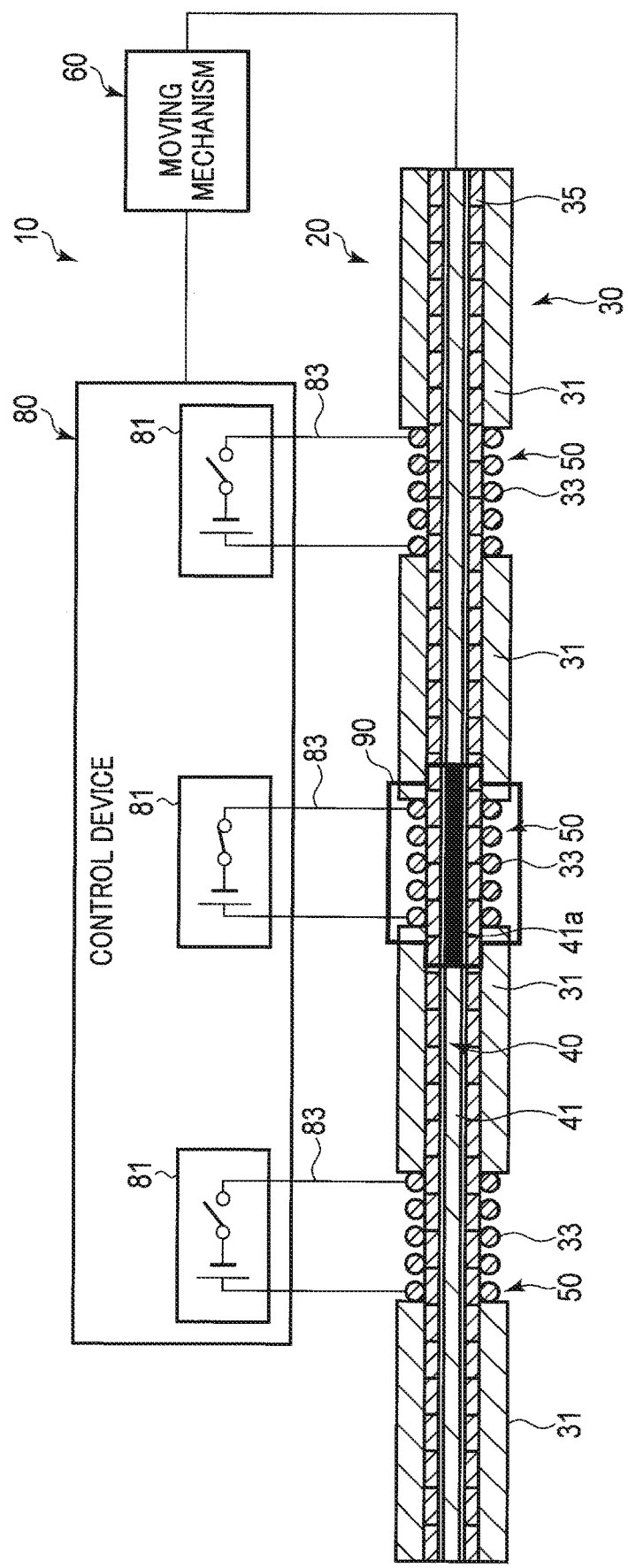
F I G. 2A

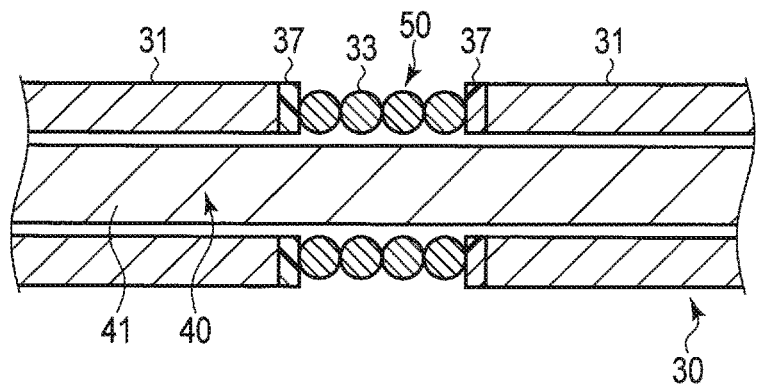
F I G. 3A
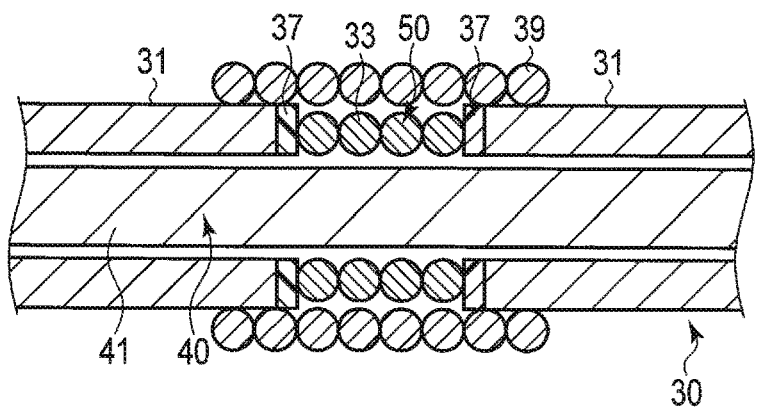
F I G. 3B
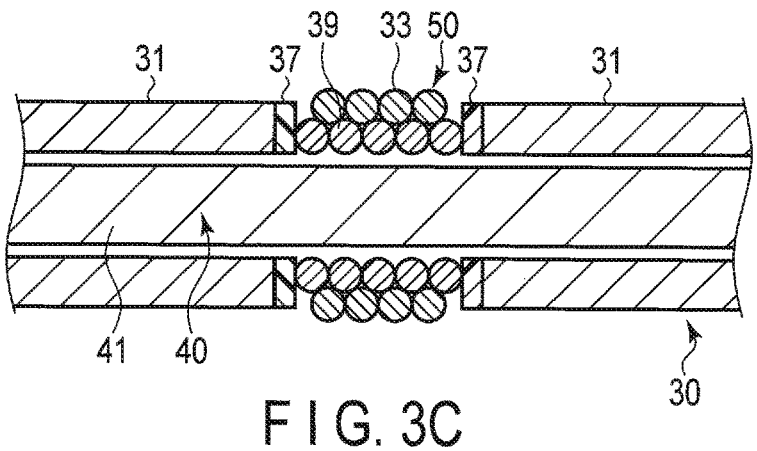
F I G. 3C

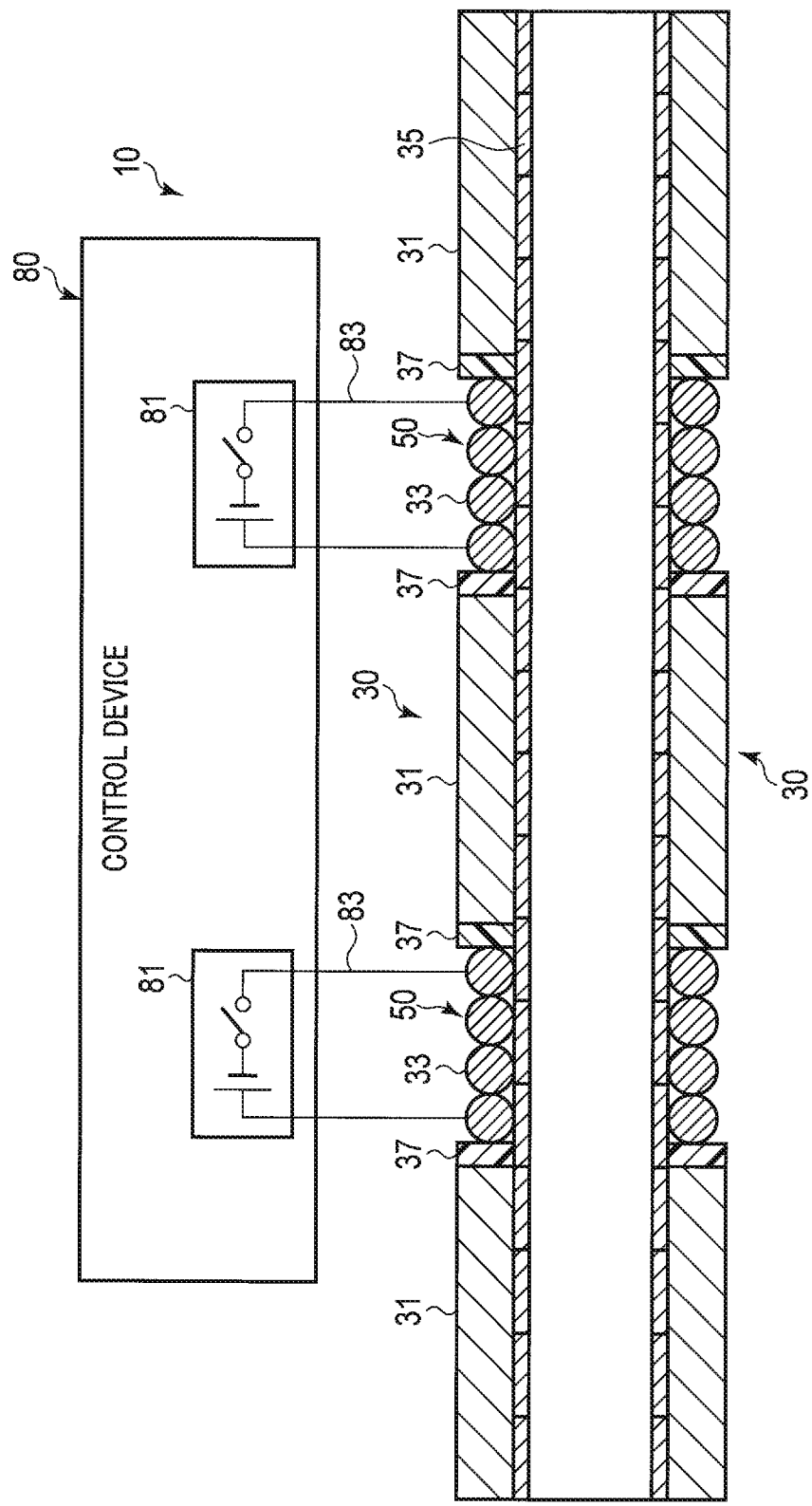
F I G. 4B

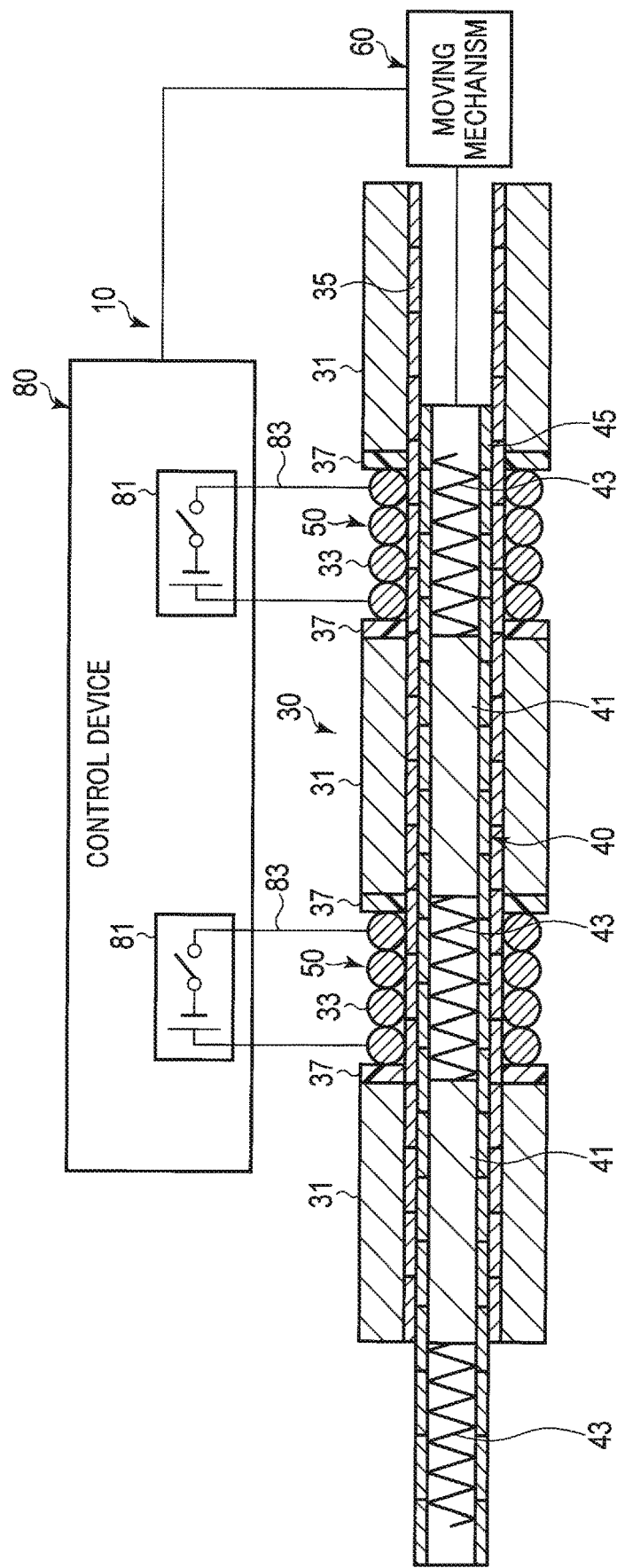
F I G. 5A

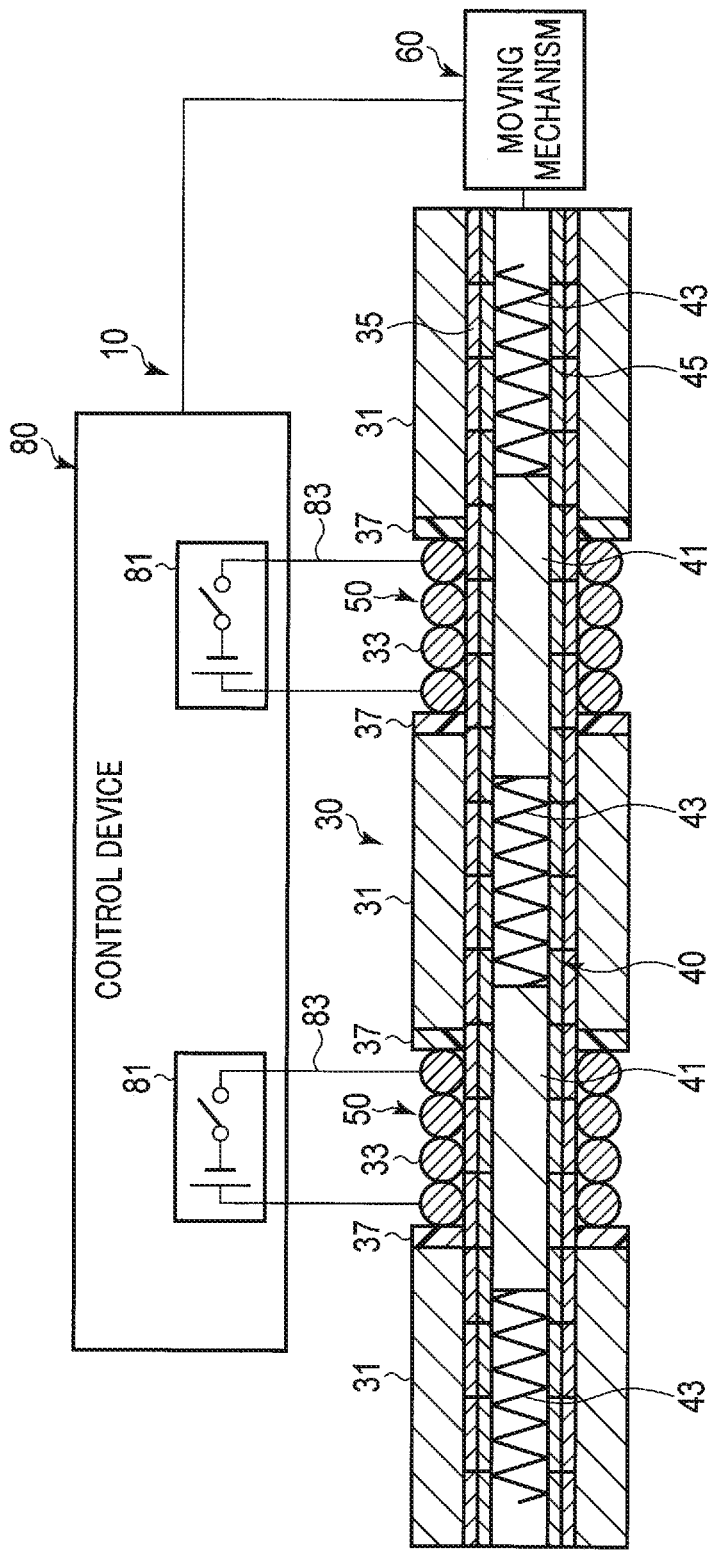
F I G. 5B

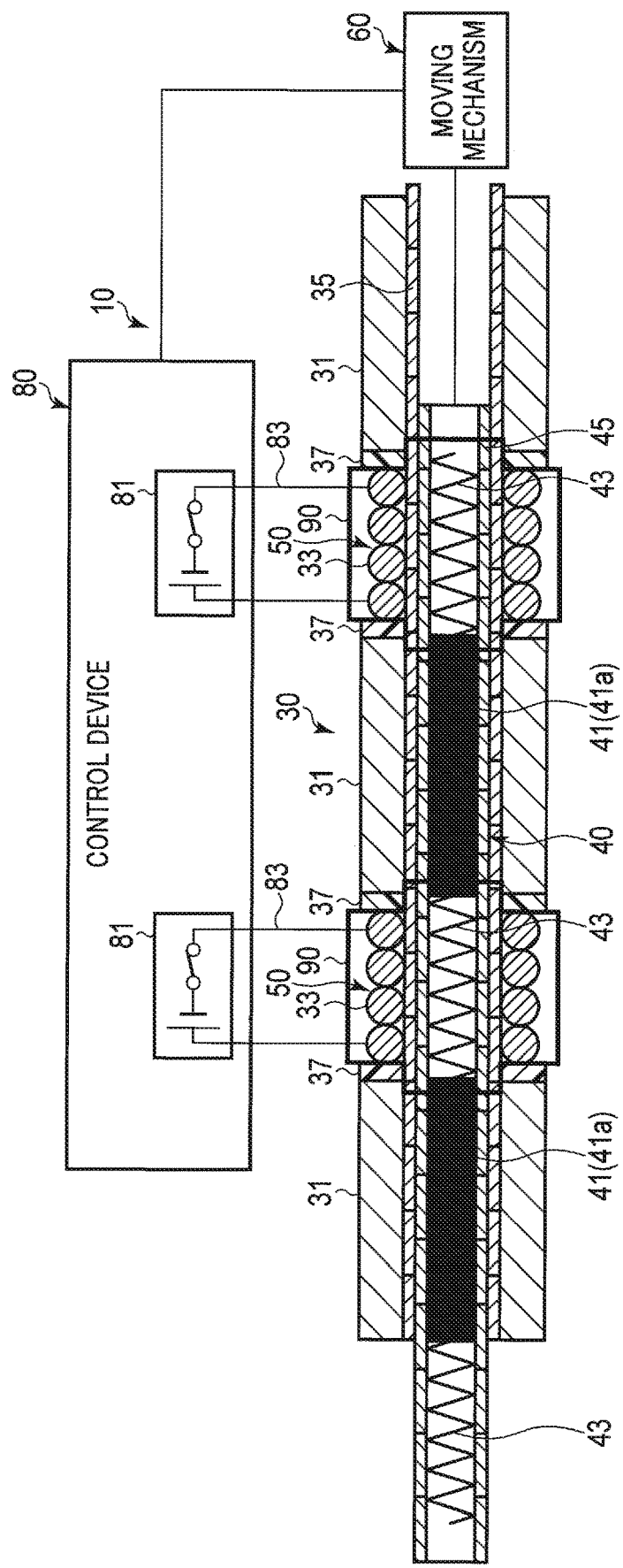
F I G. 5D

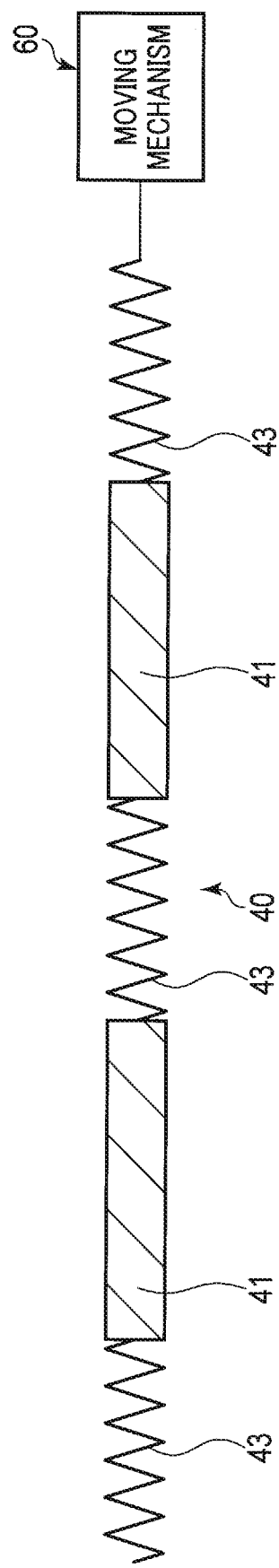
F I G. 6A

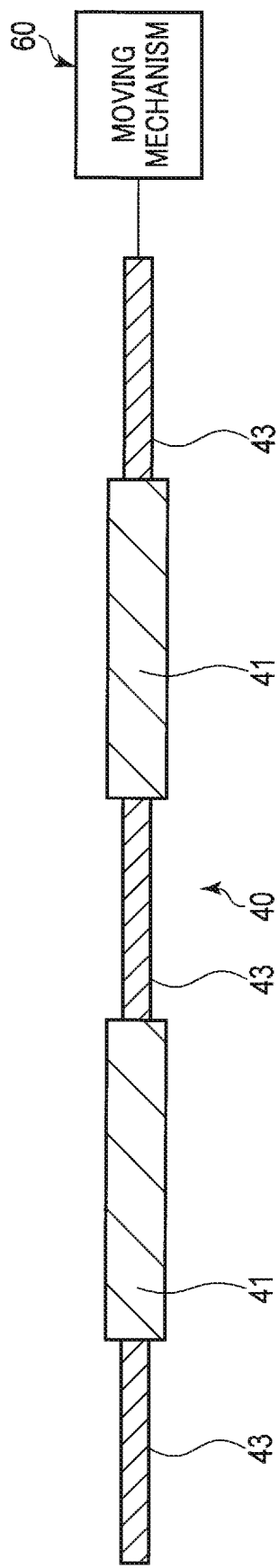
F I G. 6B

VARIABLE STIFFNESS APPARATUS

CROSS-REFERENCE TO RELATED APPLICATIONS

This application is a Continuation Application of PCT Application No. PCT/JP2016/085199, filed Nov. 28, 2016, the entire contents of which are incorporated herein by reference.

BACKGROUND OF THE INVENTION

1. Field of the Invention

The present invention relates to a variable stiffness apparatus configured to change stiffness of a flexible member.

2. Description of the Related Art

For example, Jpn. Pat. Appln. KOKAI Publication No. H5-91971 discloses an endoscope capable of changing the stiffness of a flexible section of an insertion section. In this endoscope, an end of a flexible member (for example, a coil pipe) is fixed in a predetermined position of the endoscope, and a flexibility adjustment member (for example, a flexibility adjustment wire inserted through a coil pipe) is fixed to the flexible member through a separator. The flexible member and the flexible adjustment member extend across nearly the entire body (full length) of a soft portion along the soft portion that is a member in which the flexible member and the flexible adjustment member are installed, and further extend to a control section. By pulling the flexible adjustment member, the flexible member is compressed and stiffened. In this way, the stiffness of the soft portion is changed across nearly the entire body of the soft portion.

BRIEF SUMMARY OF THE INVENTION

The present invention is directed to a variable stiffness apparatus that is to be installed in a flexible member and that is configured to provide different levels of stiffness to the flexible member. The variable stiffness apparatus includes a first elongated member, a second elongated member arranged along the first elongated member, and an inducing member. The first elongated member includes at least one high bending stiffness portion, and at least one low bending stiffness portion with a bending stiffness lower than that of the high bending stiffness portion. The second elongated member includes at least a shape memory member capable of transitioning in phase between a first phase and a second phase. The shape-memory member takes a low-stiffness state when the shape memory member is in the first phase, and takes a high-stiffness state, in which the shape-memory member has higher stiffness than in the low-stiffness state, when the shape memory member is in the second phase. The inducing member causes a region of the shape memory member that is arranged around the low bending stiffness portion to transition in phase between the first phase and the second phase, so as to change the stiffness of the region of the second elongated member in longitudinal axis direction of the second elongated member.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1B is a view showing a state in which a region of a shape memory member provided in the variable stiffness system is heated.

FIG. 2A is a view showing a state in which a region of a shape memory member provided in a variable stiffness system of a second embodiment is heated.

FIG. 3A is a view showing a first modification of the second embodiment.

FIG. 3B is a view showing a second modification of the second embodiment.

FIG. 3C is a view showing a third modification of the second embodiment.

FIG. 4B is a schematic view of a first elongated member and a control device provided in the variable stiffness system shown in FIG. 4A.

FIG. 5A is a view showing that the variable stiffness apparatus provided in the variable stiffness system shown in FIG. 4A is in a lowest-stiffness state.

FIG. 5B is a view showing that, by moving, the variable stiffness apparatus shown in FIG. 5A has switched to the low-stiffness state.

FIG. 5D is a view showing that, by moving, the variable stiffness apparatus shown in FIG. 5C has switched to the low-stiffness state.

FIG. 6A is a view showing an example of the second elongated member of the third embodiment.

FIG. 6B is a view showing an example of the second elongated member of the third embodiment.

DETAILED DESCRIPTION OF THE INVENTION

The embodiments of the present invention will be described hereinafter with reference to the drawings. It should be noted that parts of the members in some of the drawings are omitted for a better understanding of the drawings. In the shape memory member 41, a region in the high-stiffness state (rigid state), i.e., heated region 41a, is shown in black.

First Embodiment

Hereinafter, a first embodiment of the present invention will be described.

Figure 1A:
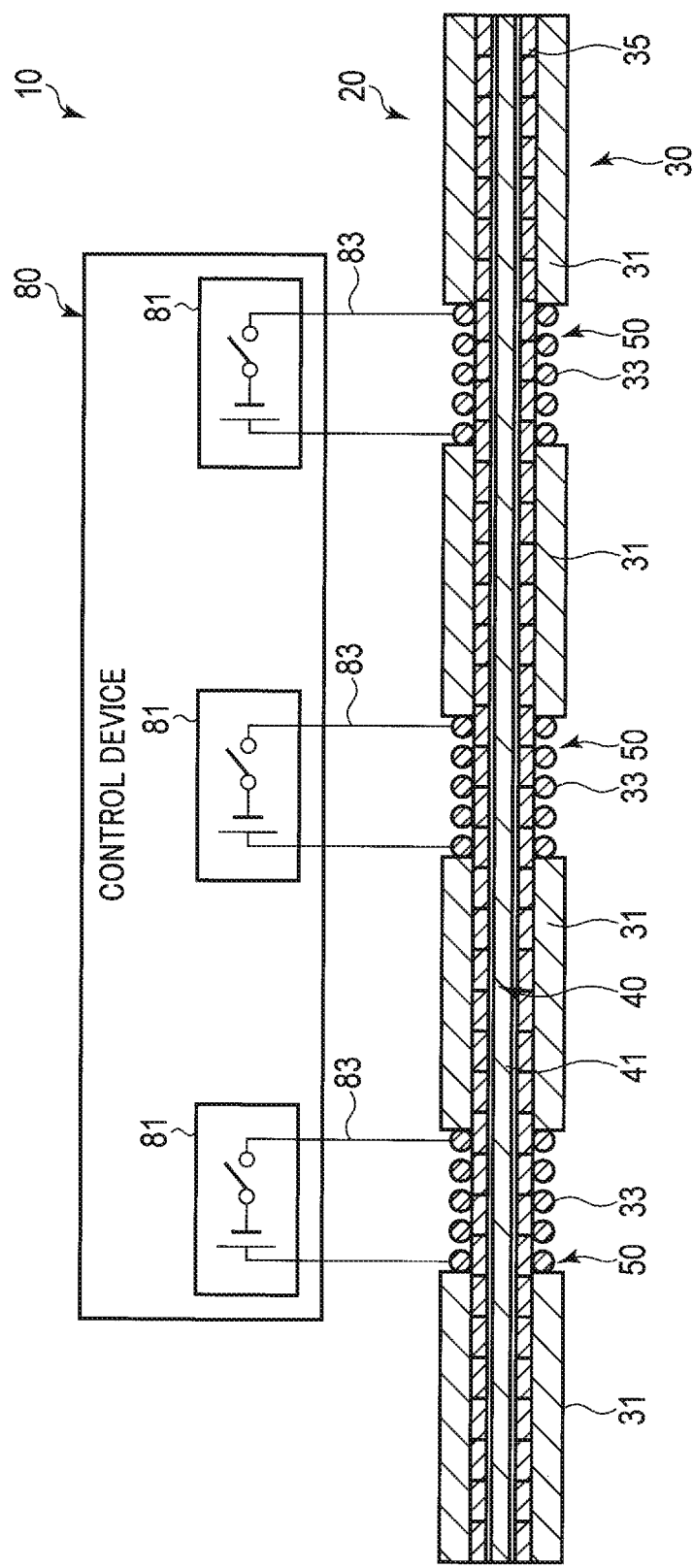
FIG. 1A is a schematic view of a variable stiffness system of a first embodiment.
Figure 1C:
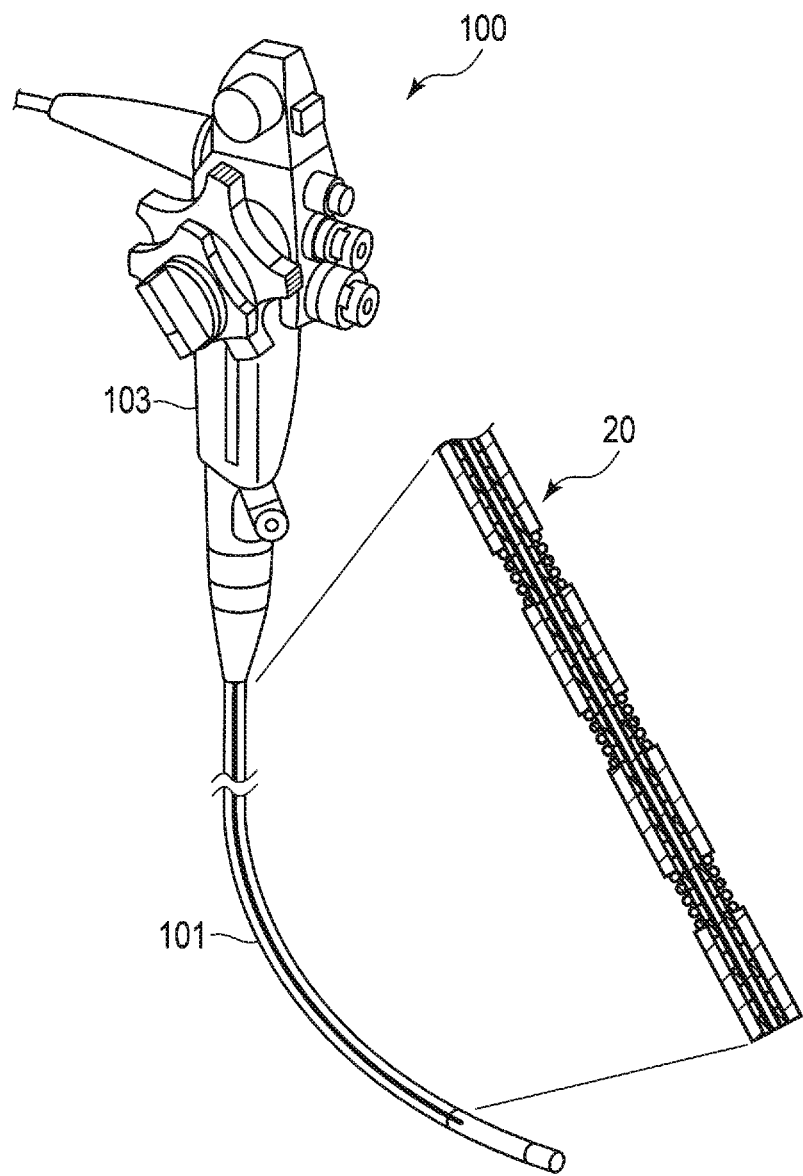
FIG. 1C is a perspective view of an endoscope incorporating a variable stiffness apparatus of the variable stiffness system.

As shown in FIGS. 1A, 1B, and 1C, a variable stiffness system 10 includes a variable stiffness apparatus 20 to be installed in a flexible member 101, for example, and a control device 80 configured to control the variable stiffness apparatus 20.

The variable stiffness apparatus 20 provides the flexible member 101 with different stiffness to change the stiffness of the flexible member 101. The variable stiffness apparatus 20 includes a first elongated member 30, a second elongated member 40 that is arranged along the first elongated member 30, and an inducing member 50. The second elongated member 40 may be adjacent to or abut the first elongated member 30. For example, the first elongated member 30 is an outer cylinder, and the second elongated member 40 is a core member arranged inside the first elongated member 30. For example, the cross-sectional shape of the outer cylinder perpendicular to the longitudinal axis of the outer cylinder is annular, and the outer periphery of the cross section of the core member perpendicular to the longitudinal axis of the core member is circular. In this case, the variable stiffness apparatus 20 provides a stable bending stiffness for bending in any direction. The cross-sectional shape of the outer cylinder does not necessarily have to be annular, and may be a different shape, for example, C-shaped. In the present embodiment, the first elongated member 30 and the second elongated member 40 are positioned and fixed in the flexible member 101. In this way, the second elongated member 40 is positioned and fixed relatively to the first elongated member 30.

The first elongated member 30 includes at least one high bending stiffness portion 31 with a relatively high bending stiffness, and at least one low bending stiffness portion 33 with a relatively low bending stiffness. In other words, the high bending stiffness portions 31 have a high bending stiffness, while the low bending stiffness portions 33 have a bending stiffness lower than the bending stiffness of the high bending stiffness portions 31. In the present embodiment, for example, the first elongated member 30 includes four high bending stiffness portions 31 and three low bending stiffness portions 33. The first elongated member 30 further includes a cylindrical outer support member 35 supporting the high bending stiffness portions 31 and the low bending stiffness portions 33. The bending stiffness of the outer support member 35 is lower than the bending stiffness of the high bending stiffness portions 31. The bending stiffness of the outer support member 35 may be the same as or different from the bending stiffness of the low bending stiffness portions 33. For this reason, the first elongated member 30 is relatively easy to bend at the low bending stiffness portions 33 and relatively hard to bend at the high bending stiffness portions 31.

The high bending stiffness portions 31, the low bending stiffness portions 33, and the outer support member 35 are separate from each other. The high bending stiffness portions 31 include a cylindrical member such as, for example, a metal pipe. The low bending stiffness portions 33 include a coil member such as, for example, a loosely wound coil. The coil member of the low bending stiffness portions 33 may be a tightly wound coil. The outer support member 35 includes, for example, a coil member such as a tightly wound coil. The coil member of the outer support member 35 may be a loosely wound coil. The low bending stiffness portions 33 and the outer support member 35 may include, for example, a helical member made of metal shaped like a wire. The high bending stiffness portions 31 are cylindrical rigid portions with a high bending stiffness, and the low bending stiffness portions 33 and the outer support member 35 are cylindrical soft portions with a low bending stiffness.

The outer support member 35 is arranged inside the high bending stiffness portions 31 and the low bending stiffness portions 33. The outer peripheral surface of the outer support member 35 is adhesively fixed to the inner peripheral surface of the high bending stiffness portions 31. The high bending stiffness portions 31 are arranged at desired intervals with respect to each other in longitudinal axis direction of the first elongated member 30. The low bending stiffness portions 33 are arranged in each space between the high bending stiffness portions 31 in longitudinal axis direction of the first elongated member 30. In this manner, the high bending stiffness portions 31 and the low bending stiffness portions 33 are alternately arranged in longitudinal axis direction of the first elongated member 30. In other words, the low bending stiffness portions 33 are not in direct mechanical contact with each other, and are arranged apart from each other. The low bending stiffness portions 33 are not in direct thermal contact with each other. The ends of each low bending stiffness portion 33 are fixed to the ends of the high bending stiffness portions 31 adjacent thereto. The ends of the low bending stiffness portion 33 may be arranged apart from the ends of the high bending stiffness portions 31 adjacent thereto. The low bending stiffness portions 33 wind around the outer support members 35 in the spaces between the high bending stiffness portions 31. In the present embodiment, a single low bending stiffness portion 33 does not wind around the outer support member 35 across the entire length of the outer support member 35, but rather winds around a region of the outer support member 35 across the entire length of the outer support member 35. Hereinafter, a region of the member around which the low bending stiffness portion 33 is wound will be referred to as the "wound portion". In the present embodiment, the wound portion indicates a region of the outer support member 35. Thus, the low bending stiffness portion 33 partially winds around the outer support member 35. In other words, the low bending stiffness portion 33 is positioned on the outer support member 35 by the high bending stiffness portions 31 so that the low bending stiffness portion 33 winds around the region of the outer support member 35. The outer diameter of the winding of the low bending stiffness portion 33 is substantially the same as the outer diameter of the high bending stiffness portions 31. It is preferable that the winding of the low bending stiffness portion 33 does not protrude with respect to the high bending stiffness portions 31 in the direction orthogonal to the longitudinal axis of the first elongated member 30. The inner peripheral surface of the low bending stiffness portion 33 contacts with the outer peripheral surface of the outer support member 35. The inner peripheral surface of the low bending stiffness portions 33 may be separated from the outer peripheral surface of the outer support member 35. The length of the low bending stiffness portion 33 is different from the length of the high bending stiffness portions 31, for example, shorter than the length of the high bending stiffness portions 31. The length of the low bending stiffness portions 33 may be the same as the length of the high bending stiffness portions 31.

The outer support member 35 is arranged across the entire length of the variable stiffness apparatus 20. The outer support member 35 is arranged in a helix. For example, the outer support member 35 functions as a core member for the high bending stiffness portions 31 and the low bending stiffness portions 33. The outer support member 35 is arranged for positioning the low bending stiffness portions 33 and the high bending stiffness portions 31, and for facilitating assembly the first elongated member 30. The outer support member 35 may be omitted, as long as the low bending stiffness portions 33 can be positioned easily with respect to the high bending stiffness portions 31.

The second elongated member 40 is arranged across the entire length of the variable stiffness apparatus 20. The second elongated member 40 is arranged inside the outer support member 35. In this way, the outer support member 35 is located between the second elongated member 40 and a series of the high bending stiffness portions 31 and the low bending stiffness portions 33 in radial direction of the second elongated member 40. The outer peripheral surface of the second elongated member 40 is not in contact with the inner peripheral surface of the outer support member 35, and a space is formed between the outer support member 35 and the second elongated member 40.

The second elongated member 40 includes at least a shape memory member 41 capable of transitioning in phase between a first phase and a second phase due to heat. In the present embodiment, the second elongated member 40 includes only the shape memory member 41. The shape memory member 41 takes a low-stiffness state in which it easily deforms by external force to exhibit a low modulus of elasticity, when the shape memory member 41 is in the first phase. Therefore, when the shape memory member 41 is in the first phase, the shape memory member 41 provides a relatively low stiffness to the flexible member 101. In the first phase, the variable stiffness apparatus 20 and the flexible member 101 can be easily bent by, for example, external force. The shape memory member 41 takes a high-stiffness state in which it has a stiffness higher than in the low-stiffness state to exhibit a high modulus of elasticity, when the shape memory member 41 is in the second phase. Therefore, when the shape memory member 41 is in the second phase, the shape memory member 41 takes the high-stiffness state in which it tends to take on a memory shape memorized in advance against external force to provide relatively high stiffness to the flexible member 101. The memorized shape may be, for example, linear. In the second phase, the variable stiffness apparatus 20 and the flexible member 101 can maintain a substantially linear state, for example, or can be bent by external force more gently than in the first phase.

Here, "external force" means a force capable of deforming the shape memory member 41, and gravity is considered as part of the external force.

When the shape memory member 41 is in the first phase, the bending stiffness of the shape memory member 41 is lower than the bending stiffness of the high bending stiffness portions 31, and is the same as or lower than the bending stiffness of the low bending stiffness portions 33. When the shape memory member 41 is in the second phase, the bending stiffness of the shape memory member 41 is the same as or lower than the bending stiffness of the high bending stiffness portions 31, and is higher than the bending stiffness of the low bending stiffness portions 33.

The shape memory member 41 includes, for example, a shape memory alloy. The shape memory alloy may be, for example, an alloy containing NiTiCu. The shape memory member 41 is not limited to the shape memory alloy, and may be made of other materials such as a shape memory polymer, a shape memory gel, a shape memory ceramic, and the like.

The shape memory alloy constituting the shape memory member 41 may be, for example, a member that transitions in phase between the martensite phase and the austenite phase. The shape memory alloy is easily plastically deformed by external force when in the martensitic phase. In other words, the shape memory alloy exhibits a low modulus of elasticity when in the martensitic phase. On the other hand, the shape memory alloy resists external force and is not easily deformed when in the austenite phase. It is herein assumed that the shape memory alloy has been deformed by a greater external force. When such greater external force against the deformed shape memory alloy is canceled, the shape memory alloy exhibits super-elasticity and returns to the memorized shape. In other words, the shape memory alloy exhibits a high modulus of elasticity when in the austenite phase.

The low bending stiffness portions 33 include a conductive material. The low bending stiffness portions 33 may be made of, for example, a heating wire, that is, a conductive member with a large electric resistance. For example, a first insulating film (not shown) is around the low bending stiffness portions 33. The first insulating film prevents short circuits between the low bending stiffness portions 33 and the outer support member 35 and between the high bending stiffness portions 31 and the low bending stiffness portions 33.

For example, a second insulating film (not shown) is around the outer support member 35. The second insulating film prevents short circuits between the low bending stiffness portions 33 and the outer support member 35, between the high bending stiffness portions 31 and the outer support member 35, and between the outer support member 35 and the shape memory member 41.

The inducing member 50 has an ability of receiving electric current from the control device 80 to generate heat. The inducing member 50 transfers the heat to a region of the shape memory member 41 around the inducing member 50. In the region, the inducing member 50 causes the phase transition of the shape memory member 41 between the first phase and the second phase. The inducing member 50 changes the stiffness of the region of the second elongated member 40 in longitudinal direction of the second elongated member 40. The inducing member 50 may be arranged at a position allowing a phase transition of the shape memory member 41 to occur. With a configuration wherein, for example, the low bending stiffness portion 33 includes the inducing member 50, the variable stiffness apparatus 20 can be configured simpler. In the present embodiment, as an example of a configuration in which the low bending stiffness portion 33 includes the inducing member 50, the low bending stiffness portion 33 doubles as the inducing member 50.

Next, phase transitions of the shape memory member 41 caused by heat will be described.

The control device 80 includes drive units 81 each configured to drive the corresponding low bending stiffness portion 33 independently. Each drive unit 81 includes a power supply and a switch. The drive unit 81 is electrically connected to the low bending stiffness portion 33 through a wiring portion 83. The wiring portion 83 includes, for example, members made of metal shaped like wires. The wiring portion 83 only needs to be electrically connected to the low bending stiffness portion 33, and may be integral with or separate from the low bending stiffness portion 33. When switching the switch on, the drive unit 81 supplies electric current through the wiring portion 83 to the low bending stiffness portion 33, and, when switching the switch off, the drive unit 81 stops the supply of electric current to the low bending stiffness portion 33.

The low bending stiffness portion 33 has an ability of receiving electric currents from the control device 80 to generate heat. The amount of heat generated by the low bending stiffness portion 33 corresponds to the amount of supplied electric current. The low bending stiffness portion 33 functions as inducing member 50 causing, due to the heat, the shape memory member 41 to transition in phase between the first phase and the second phase. More specifically, the low bending stiffness portion 33 functions as a coil heater being a heating portion configured to heat the shape memory member 41 through the outer support member 35. The shape memory member 41 has a property of transitioning from the first phase to the second phase by the heat generated by the low bending stiffness portion 33 functioning as the inducing member 50. More specifically, the low bending stiffness portion 33 functioning as the inducing member 50 causes a region of the shape memory member 41 that is arranged around the low bending stiffness portions 33 to transition in phase between the first phase and the second phase. The low bending stiffness portion 33 changes the stiffness of the region of the second elongated member 40 in longitudinal axis direction of the second elongated member 40.

Next, an area 90 heated by the low bending stiffness portion 33 will be described with reference to FIG. 1B. The area 90 indicates the periphery (near vicinity) of the low bending stiffness portion 33 as well as the area to which heat generated by the low bending stiffness portion 33 is transmitted. In the present embodiment, a bending stiffness portion 33 winds around a region (wound portion) of the outer support member 35. Therefore, instead of heating the outer support member 35 over the entire length, the low bending stiffness portion 33 heats the region (wound portion). In other words, the one low bending stiffness portion 33 partially heats the outer support member 35. The low bending stiffness portion 33 may not only heat the wound portion but also the periphery of the wound portion including the wound portion. The low bending stiffness portion 33 does not heat the shape memory member 41 across the entire length through the wound portion. Since the first elongated member 30 is positioned and fixed relatively to the second elongated member 40, the low bending stiffness portion 33 changes the stiffness of the region of the memory member 41 through the wound portion across the entire shape memory member 41. In other words, the low bending stiffness portion 33 heats a desired area of the shape memory member 41. In this way, the low bending stiffness portion 33 partially heats the shape memory member 41. More specifically, the low bending stiffness portion 33 heats the region of the shape memory member 41 surrounded by the wound portion through the wound portions.

Hereinafter, the heated region of the heated shape memory member 41, in other words, the area of the shape memory member 41 in which heating is desired, will be referred to as "heated region 41a". To distinguish the heated region 41a from the unheated regions in the shape memory member 41, the heated region 41a is shown in black in the drawings. The heated region 41a is included around the low bending stiffness portion 33. The heated region 41a may include a region surrounded by and overlapping the low bending stiffness portion 33, and the peripheries of this region. In other words, the heated region 41a includes not only a region of the shape memory member 41 surrounded by the wound portion, but also regions of the shape memory member 41 surrounded by the ends of the high bending stiffness portions 31. In other words, the heated region 41a may be slightly longer than the wound portion. The heated region 41a is a rigid portion in the second phase, whereas regions of the shape memory member 41 other than the heated region 41a are soft portions in the first phase and softer than the heated region 41a.

The heat transfer range in the wound portion is adjusted by, for example, the heat temperature, the wound portion thickness, the length and thickness of the high bending stiffness portion 31, the length and thickness of the low bending stiffness portion 33, the thermal conductivity of the outer support member 35, the thermal conductivity of the high bending stiffness portion 31, the material of the low bending stiffness portion 33, the material of the high bending stiffness portion 31, and the material of the outer support member 35. The length of the heat transfer range in the wound portion indicates the length of the first elongated member 30 in longitudinal axis direction.

The heat transfer range in the heated region 41a is adjusted by, for example, the heat temperature, the wound portion thickness, the length and thickness of the wound portion, the length and thickness of the high bending stiffness portion 31, the length and thickness of the low bending stiffness portion 33, the thickness of the heated region 41a, the thermal conductivity of the high bending stiffness portions 31, the thermal conductivity of the outer support member 35, the thermal conductivity of the shape memory member 41, the material of the high bending stiffness portion 31, the material of the low bending stiffness portion 33, the material of the outer support member 35, and the material of the shape memory member 41. The length of the heat transfer range in the heated region 41a indicates the length of the first elongated member 30 in longitudinal axis direction.

The shape memory member 41 has an elongated external shape. The low bending stiffness portions 33 each have a member shaped like a wire, and are arranged on the outer periphery of the outer support member 35 arranged on the outer periphery of the shape memory member 41. The low bending stiffness portions 33 are arranged along the longitudinal axis direction of the variable stiffness apparatus 20 at desired intervals with respect to each other. The low bending stiffness portions 33 extend spirally on the outer periphery of the outer support member 35. Due to this configuration, the heat generated from the low bending stiffness portions 33 is efficiently transferred through the outer support member 35 to the shape memory member 41.

The low bending stiffness portions 33 may have the same structure. However, without being limited thereto, the low bending stiffness portions 33 may include different structures. These different structures may have, for example, different lengths, different thicknesses, different pitches, and may be made of different materials. In other words, all or some of the low bending stiffness portions 33 may have the same or different characteristics.

Next, the relationship between the variable stiffness apparatus 20 and the flexible member 101 will be described.

The variable stiffness apparatus 20 is installed in the flexible member 101 without any restraint on the shape memory member 41. For example, the variable stiffness apparatus 20 is arranged in a limited space of the flexible member 101 with a little space. "Limited space" means a space that can just contain the variable stiffness apparatus 20. Therefore, even just a slight deformation of one of the variable stiffness apparatus 20 and the flexible member 101 can lead to a contact with the other one to exert external force thereon. The flexible member 101 only needs to have a space slightly larger than the variable stiffness apparatus 20.

For example, the flexible member 101 is a tube that has an inner diameter slightly larger than the outer diameter of the variable stiffness apparatus 20 and that can be bent by applying external force. The variable stiffness apparatus 20 may be arranged inside this tube. The variable stiffness apparatus 20 is positioned and fixed relatively to the flexible member 101. As shown in FIG. 1C, the flexible member 101 may be, for example, an insertion section of an endoscope 100. Therefore, the endoscope 100 includes the flexible member 101 and the variable stiffness apparatus 20 that is installed in the flexible member 101 and that is configured to provide different levels of stiffness to the flexible member 101. The control device 80 may be arranged in the endoscope 100 or in the control device (not shown) of the endoscope 100 that is connected to the endoscope 100. Thus, the variable stiffness system 10 is either arranged in the endoscope 100 or in an endoscope system including the endoscope 100 and the control device of the endoscope 100.

Hereinafter, the change in stiffness of the desired areas in the flexible member 101 according to the present embodiment will be described.

First, it is assumed that the variable stiffness system 10 is in an initial state, as shown in FIG. 1A. In the initial state, the drive units 81 do not supply electric current to the low bending stiffness portions 33, the low bending stiffness portions 33 do not generate heat, no heated region 41a appears, and the shape memory member 41 and the flexible member 101 are in the low-stiffness state across the entire length.

As shown in FIG. 1B, for example, when switching the switch on, the drive unit 81 supplies electric current through the wiring portion 83 to a low bending stiffness portion 33. In response to the supply of electric current, the low bending stiffness portion 33 generates heat. The heat is not directly transmitted from the low bending stiffness portion 33 to the shape memory member 41, but indirectly transmitted from the low bending stiffness portion 33 to the shape memory member 41 through the wound portion. The heat is not transmitted from the low bending stiffness portion 33 across the entire length of the outer support member 35 to the outer support member 35, but to a wound portion being a region of the outer support member 35. The heat is further transferred from the wound portion to the heated region 41a of the shape memory member 41.

The transfer of heat from the low bending stiffness portion 33 to the high bending stiffness portion 31 and from the high bending stiffness portion 31 to the outer support member 35 is suppressed by, for example, the thermal conductivity of the high bending stiffness portion 31. Adjusting the heat transfer range in the heated region 41a suppresses that the heat transferred from the wound portion to the heated region 41a is transmitted from the heated region 41a to regions of the shape memory member 41 other than the heated region 41a. In this way, adjusting the heat transfer range of a wound portion and a heated region 41a suppresses that the heat is transmitted from the wound portion across the entire length of the shape memory member 41.

By transferring heat, the temperature of the heated region 41a rises. Due to the heating, the heated region 41a switches from the first phase to the second phase and the stiffness of the heated region 41a increases. As a result, the heated region 41a switches from the low-stiffness state to the high-stiffness state. In other words, the low bending stiffness portion 33 causes the heated region 41a being a region of the shape memory member 41 that is arranged around the low bending stiffness portion 33 to transition in phase from the first phase to the second phase. The low bending stiffness portion 33 causes the heated region 41a to transition in phase from the low-stiffness state to the high-stiffness state. The heated region 41a can be seen as a rigid portion high in stiffness and hard to bend, and regions of the shape memory member 41 other than the heated region 41a can be seen as soft portions low in stiffness and easy to bend.

The variable stiffness apparatus 20 is positioned and fixed relatively to the flexible member 101, and a heated region 41a is arranged in a desired region of the flexible member 101 by positioning. The heated region 41a switches from the low-stiffness state to the high-stiffness state, so that the stiffness of the desired areas in the flexible member 101 is increased. In other words, the variable stiffness apparatus 20 provides relatively high stiffness only to a region of the flexible member 101 of the entire length of the flexible member 101. Therefore, the flexible member 101 does not transition in phase from the low-stiffness state to the high-stiffness state across the entire length of the flexible member 101, but switches partially from the low-stiffness state to the high-stiffness state. In other words, a region of the total length of the flexible member 101 switches from the low-stiffness state to the high-stiffness state. In this way, the variable stiffness apparatus 20 changes the stiffness state of the heated region 41a being a region of the shape memory member 41 that is arranged around the low bending stiffness portion 33, so as to change the stiffness of the desired areas in the flexible member 101.

A region of the flexible member 101 in the high-stiffness state tends to return to the memory shape by resisting external force acting on the flexible member 101, that is, force capable of deforming the shape memory member 41. Therefore, the region of the flexible member 101 maintains a substantially linear state.

Figure 1D:
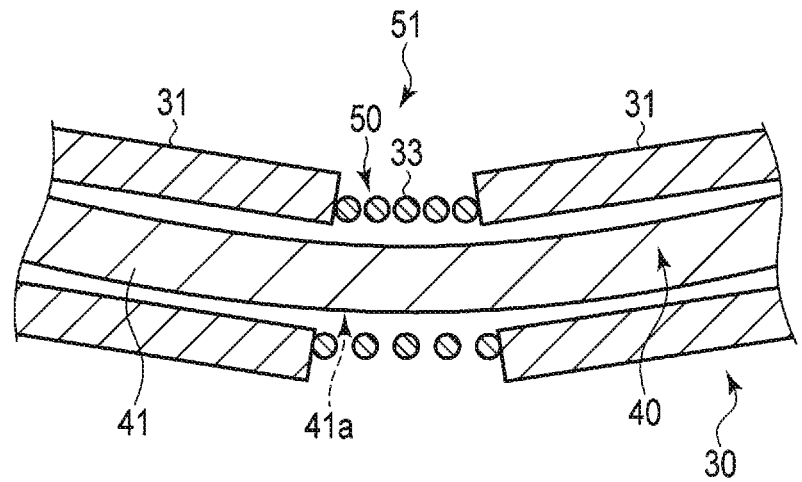
FIG. 1D is a view showing a joint of the variable stiffness apparatus in a low-stiffness state.
Figure 1E:
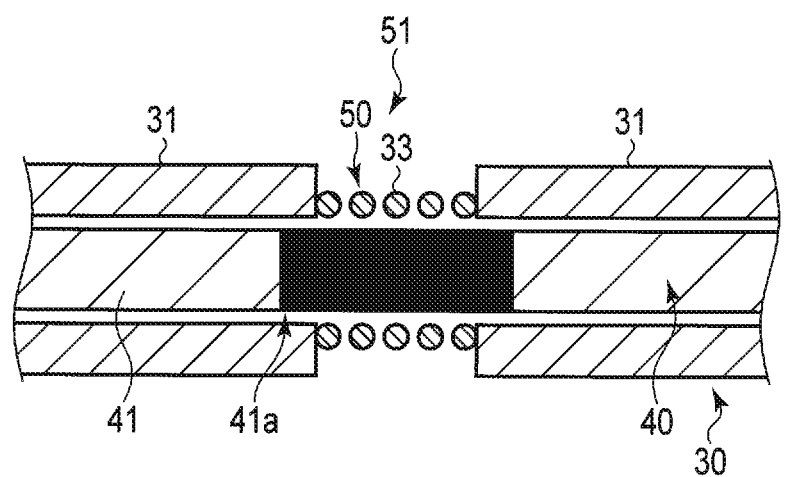
FIG. 1E is a view showing the joint of the variable stiffness apparatus in a high-stiffness state.

Here, a low bending stiffness portion 33 is sandwiched between two high bending stiffness portions 31 in longitudinal axis direction of the first elongated member 30. As shown in FIGS. 1D and 1E, the low bending stiffness portion 33 functions as a joint portion 51 of the variable stiffness apparatus 20 when one high bending stiffness portion 31 bends relative to the other high bending stiffness portion 31. In FIGS. 1D and 1E, the outer support member 35, the control device 80, the drive units 81, and the wiring portion 83 are omitted to clarify the drawings. The joint portion 51 includes the wound portion and the heated region 41a surrounded by the low bending stiffness portions 33. FIG. 1D shows the initial state, and the joint portion 51 is in the low-stiffness state. Therefore, the joint portion 51 is easily bent by external force. When the heated region 41a switches from the low-stiffness state to the high-stiffness state as shown in FIG. 1E, the joint portion 51 also switches from the low-stiffness state to the high-stiffness state. In this manner, when the joint portion 51 is in the high-stiffness state, as compared to when the joint portion 51 is in the low-stiffness state, one bending stiffness portion 31 is less likely to bend relative to the other high bending stiffness portion 31, and the substantially linear state is maintained. In other words, the variable stiffness apparatus 20 and the flexible member 101 are less likely to bend and they maintain the substantially linear state.

It is assumed that the drive unit 81 located at the rightmost position in FIG. 1B supplies electric current to the low bending stiffness portion 33 located at the rightmost position in FIG. 1B (hereinafter, for convenience, referred to as the "right side low bending stiffness portion"), and that the right side low bending stiffness portion generates heat in response to the supply of electric current. This heat is transferred from the right side low bending stiffness portion to the wound portion. Other bending stiffness portions 33 and the right side low bending stiffness portion are arranged apart from one another, and the wound portions are also arranged apart from one another. In this way, the shape memory member 41 is heated in a region (hereinafter, for convenience, referred to as the "right side heated portion") different from the above-described heated region 41a, so that the temperature of the right side heated portion rises due to the heating. As a result of heating, the right side heated portion switches from the first phase to the second phase, and the stiffness of the right side heated portion increases. In this way, the right side heated portion switches from the low-stiffness state to the high-stiffness state, the stiffness of another desired area in the flexible member 101 increases, so that two regions across the entire length of the flexible member 101 transition in phase from the low-stiffness state to the high-stiffness state.

For example, the temperature of the right side heated portion may be different from the temperature of the heated region 41a, and therefore the stiffness of the right side heated portion may be different from the stiffness of the heated region 41a. As a result, the stiffness of the other desired area of the flexible member 101 is different from the stiffness of the desired area of the flexible member 101. In this way, the stiffness of the flexible member 101 may be changed partially. Of course, in the present embodiment, when electric current flows through all the low bending stiffness portions 33, for example, the heated regions 41a can be thermally connected to each other by adjusting the heat transfer range. In this way, it is also possible to change the stiffness of the entire shape memory member 41.

When switching the switch off, the drive unit 81 stops the supply of current to the low bending stiffness portion 33. This stops the heating, so that the temperature of the heated region 41a drops due to natural cooling. Then, the heated region 41a switches from the second phase to the first phase, so that the stiffness of the heated region 41a decreases. Also, the stiffness of the region of the flexible member 101 in which the heated region 41a is arranged decreases. In other words, the variable stiffness apparatus 20 provides relatively low stiffness to the flexible member 101, and deforms easily according to external force acting on the flexible member 101, that is, force capable of deforming the shape memory member 41. In this way, the flexible member 101 can be easily bent by external force. Also, the stiffness of the heated region 41a and the stiffness of the region of the flexible member 101 can return to the stiffness prior to the heating. When the joint portion 51 is in the low-stiffness state, as compared to when it is in the high-stiffness state, one high bending stiffness portion 31 is easily bent with respect to the other high bending stiffness portion 31. In other words, the variable stiffness apparatus 20 and the flexible member 101 are easily bent.

Switching a region of the shape memory member 41 in this manner between the first phase and the second phase by the low bending stiffness portion 33, for example, switches stiffness of a desired area in the flexible member 101.

In the present embodiment, the low bending stiffness portions 33 change the stiffness of regions of the shape memory member 41 that are arranged around the low bending stiffness portions 33. In the present embodiment, the stiffness of the desired areas of the flexible member 101 can be changed by changing the stiffness of those regions. Further, in the present embodiment, providing the high bending stiffness portions 31, the low bending stiffness portions 33, the outer support member 35, and the shape memory member 41 allow the configuration of the variable stiffness apparatus 20 to be simpler and thinner, thereby allowing the flexible member 101 to be thinner.

In the present embodiment, the outer support member 35 can improve assemblability of the first elongated member 30. In the present embodiment, since the low bending stiffness portions 33 function as the inducing member 50, the configuration of the variable stiffness apparatus 20 can be simplified.

In the present embodiment, the high bending stiffness portions 31 are provided. Therefore, even if the low bending stiffness portions 33 and the heated regions 41a are short and the short heated regions 41a are in the high-stiffness state, most of the total length of the variable stiffness apparatus 20 and the flexible member 101 can be switched to the high-stiffness state by the high bending stiffness portions 31. When most of the total length of the variable stiffness apparatus 20 and the flexible member 101 is switched to the high-stiffness state, power can be saved.

In addition to switching stiffness, the variable stiffness apparatus 20 also functions as a bi-directional actuator configured to switch the shape of the flexible member 101 under the condition of external force other than gravity acting on the flexible member 101. The variable stiffness apparatus 20 further functions as a uni-directional actuator configured to restore the shape of the flexible member 101 under the condition of no external force other than gravity acting on the flexible member 101 and under the condition of the flexible member 101 being deformed in the first phase prior to the shape memory member 41 switching to the second phase.

Modifications

Figure 1F:
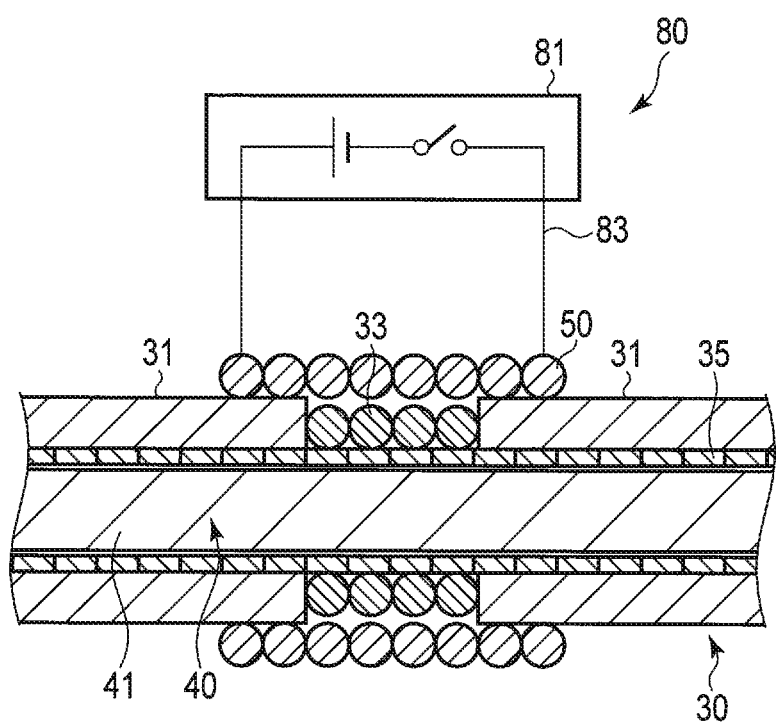
FIG. 1F is a view showing a modification of the first embodiment.

FIG. 1F shows a first modification of the present embodiment. In the present modification, as an example of a configuration in which the low bending stiffness portions 33 include the inducing members 50, the inducing members 50 are separate from the low bending stiffness portions 33. The inducing members 50 are arranged around the low bending stiffness portions 33, respectively. An inducing member 50 may be arranged across the entire length of the first elongated member 30.

The inducing member 50 includes a coil member such as a tightly wound coil, for example. The coil member of the inducing member 50 may be a loosely wound coil. The inducing member 50 may include, for example, a helical member made of metal shaped like a wire. The inducing member 50, for example, winds around the outer periphery of the low bending stiffness portion 33. The inducing member 50 may include a soft cylindrical member such as a pipe. The inducing member 50 is a cylindrical soft portion with a low bending stiffness. The bending stiffness of the inducing member 50 may be, for example, the same as or different from the bending stiffness of the low bending stiffness portion 33. The inducing member 50 may surround the entire outer periphery of the low bending stiffness portion 33.

The inner peripheral surface of the inducing member 50 is separated from the outer peripheral surface of the low bending stiffness portion 33. The inner peripheral surface of the inducing member 50 may be in close contact with the outer peripheral surface of the low bending stiffness portion 33. Both ends of the inducing member 50 may surround the outer peripheral surface of the ends of the high bending stiffness portions 31. The inner peripheral surfaces at the both ends of the inducing member 50 can be in close contact with the outer peripheral surfaces at the ends of the high bending stiffness portions 31. In other words, the inner peripheral surface at both ends of the inducing member 50 may not be in close contact with the outer peripheral surfaces at the ends of the high bending stiffness portions 31.

The inducing member 50 is electrically connected to the wiring portion 83. When switching the switch on, the drive units 81 supplies electric current through the wiring portion 83 to the inducing member 50, and, when switching the switch off, the drive units 81 stops the supply of electric current to the inducing member 50. The inducing member 50 transfers heat through the low bending stiffness portion 33 and the outer support member 35 to a region of the shape memory member 41. The inducing member 50 functions as a coil heater that is a heating portion heating the shape memory member 41 through the low bending stiffness portion 33 and the outer support member 35. As long as the inducing member 50 can heat the shape memory member 41 through the low bending stiffness portion 33 and the outer support member 35, the inducing member 50 may be in direct mechanical contact with the low bending stiffness portions 33 or may not be in direct mechanical contact with the low bending stiffness portion 33.

The configuration of the present modification may be incorporated into the configuration of each of second and third embodiments described further below, and into the configuration of each of the modifications of the second embodiment.

Second Embodiment

Hereinafter, a second embodiment of the present invention will be described with reference to FIGS. 2A and 2B. In the present embodiment, only what is different from the first embodiment will be described.

In the present embodiment, the length of each high bending stiffness portion 31 is preferably longer than the length of each heated region 41a.

The variable stiffness apparatus 20 includes a moving mechanism 60 configured to move the second elongated member 40 along the first elongated member 30. In this way, in the present embodiment, the second elongated member 40 is movable relative to the first elongated member 30. The first elongated member 30 is positioned and fixed in the same manner as in the first embodiment. The moving mechanism 60 moves, for example, the second elongated member 40 relative to the outer support member 35. The moving mechanism 60 pulls or pushes the second elongated member 40. As the second elongated member 40 moves, the heated region 41a also moves.

The moving mechanism 60 is electrically connected to the control device 80, and the movement is controlled in advance by the control device 80. For example, the moving mechanism 60 moves the heated region 41a around the high bending stiffness portion 31, the heated region 41a being a region of the shape memory member 41 in the high-stiffness state that is arranged around the low bending stiffness portion 33. The periphery of the high bending stiffness portion 31 indicates the position where the heated region 41a is surrounded by the high bending stiffness portion 31 across the entire length of the heated region 41a as shown in FIG. 2b, and where the heated region 41a overlaps the high bending stiffness portion 31 across the entire length of the heated region 41a.

For example, the moving mechanism 60 includes a motor (not shown) and a migratory member (not shown) that is connected to an end of the second elongated member 40 and configured to move the second elongated member 40 by the rotational force of the motor. The migratory member is, for example, directly connected to the end of the shape memory member 41. The migratory member is, for example, a member shaped like a wire. The moving mechanism 60 may be provided in a control section 103 connected to the proximal end of the insertion section. The moving mechanism 60 may be driven by operating the button of the control section 103.

Figure 2B:
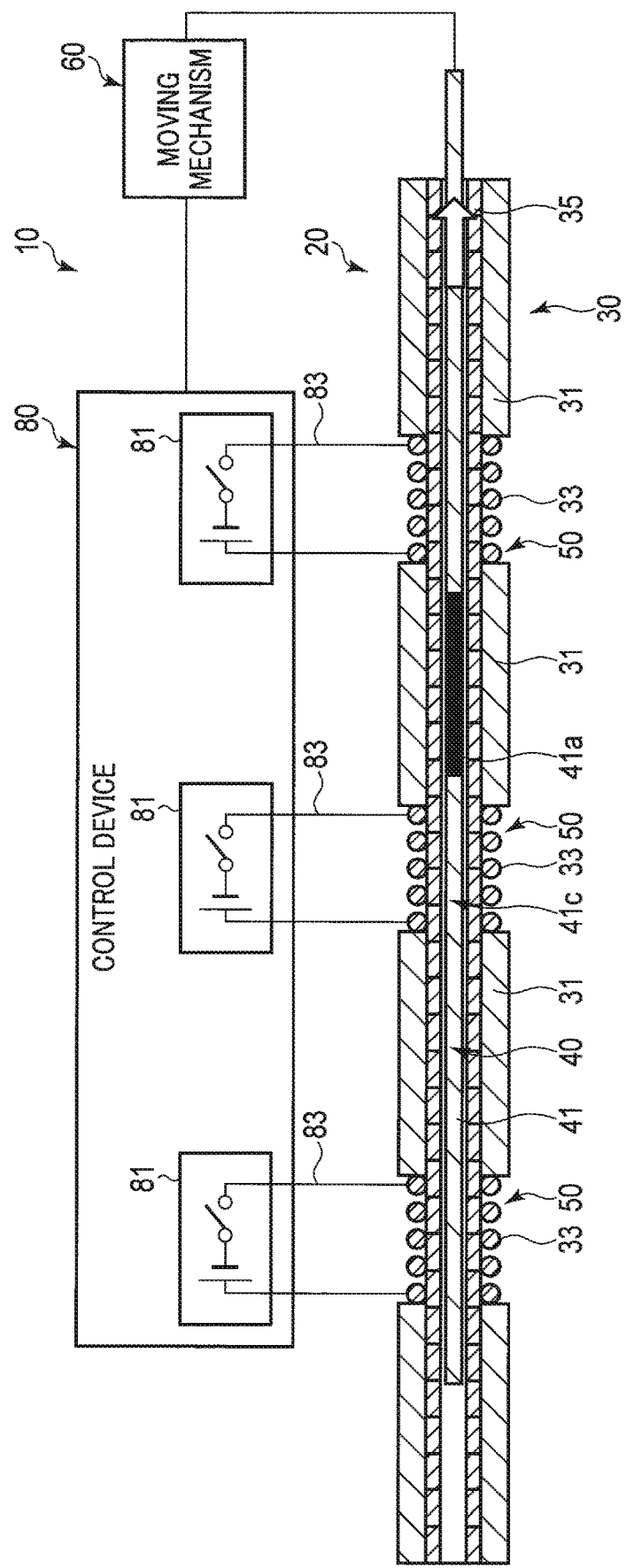
FIG. 2B is a view showing a state in which the heated region has been moved by the moving mechanism from the state shown in FIG. 2A.

Here, as shown in FIG. 2A, it is assumed that, as in the first embodiment, the stiffness of a heated region 41a around the low bending stiffness portion 33 increases by heating, and that the heated region 41a switches from the low-stiffness state to the high-stiffness state. The heated region 41a can be regarded as a rigid portion with a high stiffness. As shown in FIG. 2B, when the second elongated member 40 is moved by the moving mechanism 60, the heated region 41a that is a rigid portion shifts from the periphery of the low bending stiffness portion 33 to the periphery of the high bending stiffness portion 31. In other words, the heated region 41a overlaps the high bending stiffness portion 31. Due to the movement of the second elongated member 40, a soft region 41c that is a region of the shape memory member 41 other than the heated region 41a is arranged around the low bending stiffness portion 33 where the heated region 41a has been arranged. In other words, the soft region 41c overlaps the low bending stiffness portion 33. Yet in other words, a region of the shape memory member 41 that is arranged around the low bending stiffness portions 33 switches from the heated region 41a being a rigid portion hard to bend to the soft region 41c easy to bend. Also, the joint portion 51 switches from the high-stiffness state to the low-stiffness state. In this manner, the variable stiffness apparatus 20 provides relatively low stiffness to the flexible member 101.

Here, unlike the present embodiment, the condition in which the variable stiffness apparatus 20 provides relatively low stiffness to the flexible member 101 by natural cooling of the heated region 41a that is arranged around the low bending stiffness portions 33 will be referred to as the "natural condition". In the present embodiment, the variable stiffness apparatus 20 can provide relatively low stiffness to the flexible member 101 quicker than under the natural condition due to the movement of the heated region 41a. In other words, in the present embodiment, the flexible member 101 can be switched from the high-stiffness state to the low-stiffness state in a shorter time than by natural cooling. This improves responsiveness to the flexible member 101.

First modification

FIG. 3A shows a first modification of the present embodiment. In the present modification, the outer support member 35 is omitted. The first elongated member 30 includes heat insulating members 37, each arranged between the high bending stiffness portion 31 and the low bending stiffness portion 33 in longitudinal axis direction of the first elongated member 30. Each heat insulating member 37 is, for example, fixed to the end of the high bending stiffness portion 31 and has a ring shape. The low bending stiffness portion 33 is sandwiched between two heat insulating members 37 in longitudinal direction of the first elongated member 30. The heat insulating member 37 is fixed to the end of the low bending stiffness portion 33 and is thermally connected to the low bending stiffness portion 33. The heat insulating member 37 prevents heat generated by the low bending stiffness portion 33 from being transmitted to the high bending stiffness portion 31. The heat insulating member 37 is a member with a low thermal conductivity, such as a resin, for example.

In the present modification, the low bending stiffness portion 33 can be fixed to the high bending stiffness portion 31 by the heat insulating member 37, so that the outer support member 35 can be omitted, which allows the variable stiffness apparatus 20 to be thinner. In the present embodiment, since the outer support member 35 is unnecessary, the low bending stiffness portion 33 can be arranged closer to the shape memory member 41 than in the configuration of the first embodiment, so that the heat can be quickly transferred directly from the low bending stiffness portion 33 to the shape memory member 41. Also, since the heat insulating member 37 can prevent transmission of heat from the low bending stiffness portion 33 to the high bending stiffness portion 31, the length of the heat transmission range in the heated region 41a, that is, the length of the desired area in the flexible member 101 can be controlled more precisely.

Second modification

FIG. 3B shows a second modification of the present embodiment. The first elongated member 30 includes cylindrical connecting members 39, each connecting the high bending stiffness portions 31 with each other. Both ends of the connecting member 39 are fixed to the outer peripheral surfaces of the ends of the high bending stiffness portions 31. The connecting member 39 is arranged around each space between the high bending stiffness portions 31. A single connecting member 39 may be arranged across the entire length of the first elongated member 30. The connecting member 39 ha a bending stiffness lower than the bending stiffness of the high bending stiffness portions 31. The bending stiffness of the connecting member 39 may be the same as or different from the bending stiffness of the low bending stiffness portion 33. The connecting member 39 includes a coil member such as a tightly wound coil, for example. The coil member of the connecting member 39 may be a loosely wound coil. The connecting member 39 may include a helical member made of metal shaped like a wire, for example. In the present modification, the connecting member 39 is arranged on the outer periphery of the low bending stiffness portion 33. The connecting member 39 has a spiral shape winding around the low bending stiffness portion 33. The outer peripheral surface of the low bending stiffness portion 33 may be fixed to the inner peripheral surface of the connecting member 39.

In the present modification, the low bending stiffness portion 33 can be provided closer to the shape memory member 41 than in the configuration of the first embodiment, so that the connecting member 39 can improve connection strength of the high bending stiffness portions 31 and assemblability of the first elongated member 30.

Third Modification

FIG. 3C shows a third modification of the present embodiment. A connecting member 39 is arranged on the inner periphery of a low bending stiffness portion 33. Both ends of the connecting member 39 are fixed to the heat insulating members 37 arranged at the ends of the high bending stiffness portions 31. The inner peripheral surface of the low bending stiffness portion 33 is fixed to the outer peripheral surface of the connecting member 39, and the ends of the low bending stiffness portion 33 are arranged away from the heat insulating member 37. The heat insulating members 37 prevent heat from being transmitted from the low bending stiffness portions 33 through the connecting member 39 to the high bending stiffness portions 31.

In the present modification, the connecting member 39 can improve connection strength of the high bending stiffness portions 31 and assemblability of the first elongated member 30.

Each of the first, second, and third modifications of the second embodiment may be incorporated into the configuration of the first embodiment and into the configuration of the modification of the first embodiment.

Third Embodiment

Hereinafter, a third embodiment of the present invention will be described with reference to FIGS. 4A, 4B, and 4C. In the present embodiment, only what is different from the first and second embodiments will be described.

Figure 4A:
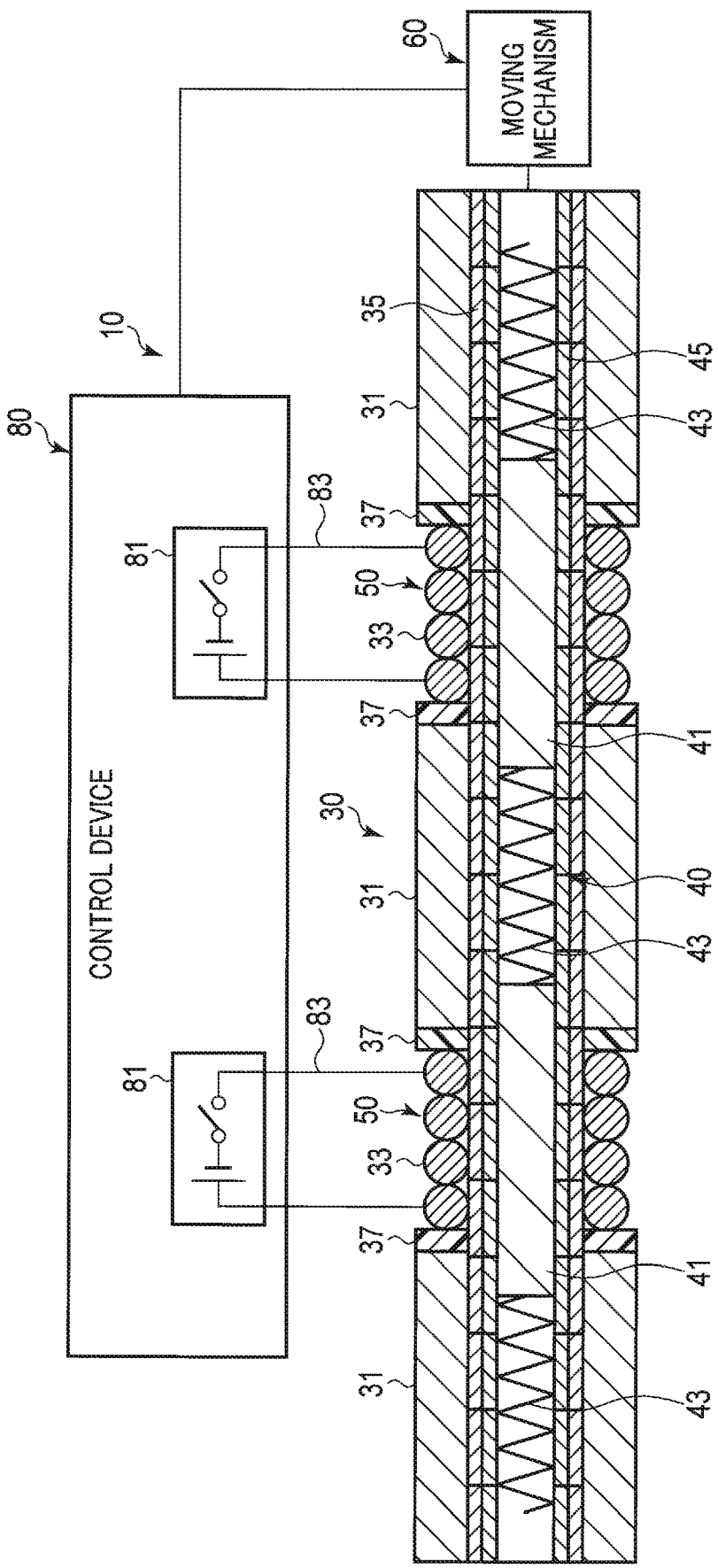
FIG. 4A is a schematic view of a variable stiffness system of a third embodiment.

As shown in FIGS. 4A and 4B, in the configuration of the first elongated member 30 of the present embodiment, the heat insulating members 37 of the first modification of the second embodiment are arranged on the first elongated member 30 of the first embodiment. The length of the high bending stiffness portions 31 is the same as the length of heated regions 41a, but preferably longer than the length of the heated regions 41a. In the present embodiment, it is assumed that three high bending stiffness portions 31 and two low bending stiffness portions 33 are provided.

Figure 4C:
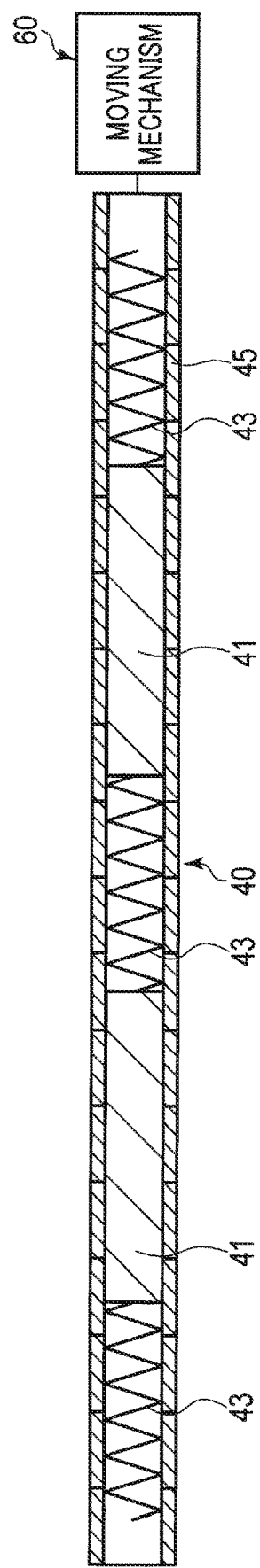
FIG. 4C is a schematic view of a second elongated member and a moving mechanism provided in the variable stiffness system shown in FIG. 4A.

As shown in FIGS. 4A and 4C, the second elongated member 40 of the present embodiment includes at least one shape memory member 41, at least one soft member 43 softer than the shape memory member 41, and a cylindrical inner support member 45 supporting the shape memory member 41 and the soft member 43. In this embodiment, for example, the second elongated member 40 includes two shape memory members 41, three soft members 43, and one inner support member 45.

The shape memory members 41 and the soft members 43 are alternately arranged in longitudinal axis direction of the second elongated member 40. In other words, the shape memory members 41 are arranged apart from each other. The shape memory members 41 and the soft members 43 are fixed to each other. The shape memory members 41 and the soft members 43 are inserted into the inner support member 45. The outer peripheral surface of the shape memory members 41 and the outer peripheral surface of the soft members 43 are fixed to the inner peripheral surface of the inner support member 45 by adhesion or welding. The shape memory members 41 and the soft members 43 are positioned and fixed to the inner support member 45.

Whether the shape memory members 41 are in the first phase or in the second phase, the bending stiffness of the shape memory members 41 is higher than the bending stiffness of the soft members 43. The shape memory members 41 function as heated regions 41a across the entire length of the shape memory members 41. The length of the shape memory members 41 is longer than the length of the low bending stiffness portions 33.

The soft members 43 are, for example, bendable spring materials. The soft members 43 are softer and more bendable than the shape memory member 41.

The inner support member 45 is arranged on the outer periphery of the shape memory members 41 and the soft members 43. The inner support member 45 includes, for example, a coil member such as a tightly wound coil. The coil member of the inner support member 45 may be a loosely wound coil. The inner support member 45 may include, for example, a helical member made of metal shaped like a wire. For example, the bending stiffness of the inner support member 45 is substantially the same as the bending stiffness of the soft members 43. The outer peripheral surface of the inner support member 45 is in contact with the inner peripheral surface of the outer support member 35, and the inner support member 45 is slid inside the outer support member 35 by the moving mechanism 60. Since the shape memory members 41 and the soft members 43 are fixed to the inner support member 45, the shape memory members 41 and the soft members 43 move together with the inner support member 45 as the inner support member 45 moves. As long as the inner support member 45 can move relative to the outer support member 35, the outer peripheral surface of the inner support member 45 does not have to be in contact with the inner peripheral surface of the outer support member 35, and a space may be formed between the outer peripheral surface of the inner support member 45 and the inner peripheral surface of the outer support member 35.

FIG. 5A shows the variable stiffness apparatus 20 in a lowest-stiffness state (super soft state). It is assumed that, in the lowest-stiffness state, the variable stiffness system 10 is in the initial state, the drive units 81 do not supply electric current to the low bending stiffness portions 33, the low bending stiffness portions 33 do not generate heat, and the shape memory members 41 and the flexible member 101 are in the low-stiffness state.

In the lowest-stiffness state, the shape memory members 41 (soft portions) overlap the high bending stiffness portions 31 (rigid portions), and the soft members 43 overlap the low bending stiffness portions 33 (soft portions). In this way, the variable stiffness apparatus 20 provides the flexible member 101 with the lowest stiffness.

FIG. 5B shows that the variable stiffness apparatus 20 is in the low-stiffness state (soft state). In this state, the second elongated member 40 is moved by the moving mechanism 60 with respect to, for example, the lowest-stiffness state.

In the low-stiffness state, the shape memory members 41 (soft portions) overlap the low bending stiffness portions 33 (soft portions), and the soft members 43 overlap the high bending stiffness portions 31 (rigid portions). In this way, the variable stiffness apparatus 20 provides the flexible member 101 with relatively low stiffness.

Figure 5C:
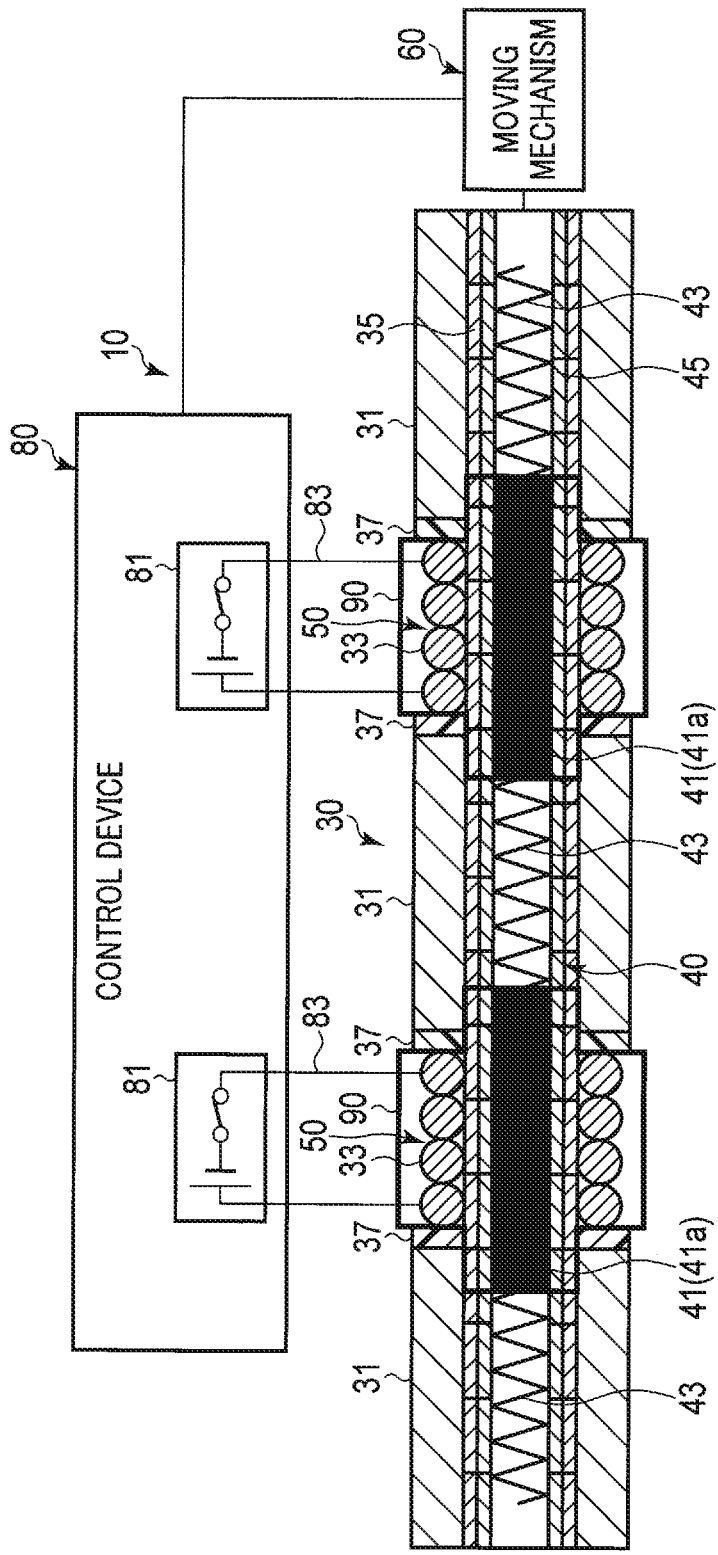
FIG. 5C is a view showing that, by heating, the variable stiffness apparatus shown in FIG. 5B has switched to the high-stiffness state.

FIG. 5C shows that the variable stiffness apparatus 20 is in the high-stiffness state (rigid state). In this state, the second elongated member 40 has not moved relative to the low-stiffness state shown in FIG. 5B. Further, due to heat generated from the low bending stiffness portions 33, the entire shape memory members 41 function as the heated regions 41a and change from the soft portions to the rigid portions.

In the high-stiffness state, the heated regions 41a (rigid portions) overlap the low bending stiffness portions 33 (soft portions), and the soft members 43 overlap the high bending stiffness portions 31 (rigid portions). Thus, the variable stiffness apparatus 20 provides the flexible member 101 with the highest stiffness.

FIG. 5D shows that the variable stiffness apparatus 20 is in the lowest-stiffness state. In this state, the second elongated member 40 is moved by the moving mechanism 60 with respect to the high-stiffness state, for example.

In the lowest-stiffness state, the heated regions 41a (rigid portions) overlap the high bending stiffness portions 31 (rigid portions), and the soft members 43 overlap the low bending stiffness portions 33 (soft portions). In this way, the variable stiffness apparatus 20 provides the flexible member 101 with the lowest stiffness.

In the present embodiment, the second elongated member 40 can be partially softened by the soft members 43. Also, the shape memory members 41 are arranged apart from each other. In this manner, transfer of heat between the shape memory members 41 is suppressed. In this way, changes in stiffness in the desired areas in the flexible member 101 can be precisely controlled.

In the present embodiment, as long as the shape memory members 41 and the soft members 43 are fixed to each other at the end portions by welding or adhesion, the inner support member 45 may be omitted. In other words, as shown in FIGS. 6A and 6B, the second elongated member 40 may include the shape memory members 41 and the soft members 43. The soft members 43 are also stretchable in the longitudinal axis direction of the second elongated member 40, for example. This allows the variable stiffness apparatus 20 and the flexible member 101 to be made thinner. Also, the bending stiffness of the soft members 43 needs to be lower than the bending stiffness of the shape memory members 41. Thus, as shown in FIG. 6B, the soft members 43 may be, for example, a metal member shaped like a wire. In FIGS. 6A and 6B, the moving mechanism 60 is connected to the soft member 43, for example.

The present invention is not limited to the above embodiments as are, and as long as the present invention does not depart from the scope of the invention, the constituent elements can be modified at the implementation stage. Furthermore, various inventions can be devised by appropriately combining the components disclosed in the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness apparatus for use in a flexible member, the variable stiffness apparatus being configured to provide different levels of stiffness to the flexible member, the variable stiffness apparatus comprising:
   a first elongated member including at least one high bending stiffness portion, and at least one low bending stiffness portion with a bending stiffness lower than that of the at least one high bending stiffness portion,
   a second elongated member arranged along the first elongated member, the second elongated member including at least a shape memory material capable of transitioning in phase between a first phase and a second phase, the shape-memory material taking a low-stiffness state when the shape memory material is in the first phase, and taking a high-stiffness state, in which the shape-memory material has a higher stiffness than in the low-stiffness state, when the shape memory material is in the second phase, and
   a heater configured to heat a region of the shape memory material that is arranged around the at least one low bending stiffness portion to cause the region of the shape memory material that is arranged around the at least one low bending stiffness portion to transition in phase between the first phase and the second phase, so as to change the stiffness of the region of the second elongated member in a longitudinal axis direction of the second elongated member.

2. The variable stiffness apparatus according to claim 1, wherein the at least one low bending stiffness portion comprises a portion of the heater.

3. The variable stiffness apparatus according to claim 2, further comprising an actuator configured to move the second elongated member relative to the first elongated member, the actuator moving the region of the shape memory material in the high-stiffness state that is arranged around the at least one low bending stiffness portion to be arranged around the at least one high bending stiffness portion.

4. The variable stiffness apparatus according to claim 3, wherein the first elongated member is an outer cylinder, the at least one high bending stiffness portion includes a cylindrical member, and the at least one low bending stiffness portion includes a coil member, and
wherein the second elongated member is a core member arranged inside the first elongated member.

5. The variable stiffness apparatus according to claim 4, wherein the at least one high bending stiffness portion of the first elongated member includes a plurality of high bending stiffness portions and the at least one low bending stiffness portion of the first elongated member includes a plurality of low bending stiffness portions each with a bending stiffness lower than that of each of the plurality of high bending stiffness portions, and
wherein the plurality of high bending stiffness portions and the plurality of low bending stiffness portions are alternately arranged in the longitudinal axis direction.

6. The variable stiffness apparatus according to claim 1, wherein the second elongated member includes only the shape memory material.

7. The variable stiffness apparatus according to claim 1, wherein the shape memory material comprises a plurality of shape memory materials and the second elongated member further comprises the plurality of shape memory materials and a plurality of soft members each softer than each of the plurality of shape memory materials, and
wherein the plurality of shape memory materials and the plurality of soft members are alternately arranged in the longitudinal direction.

8. The variable stiffness apparatus according to claim 7, wherein the second elongated member includes an inner support member that is arranged on an outer periphery of the plurality of shape memory material and the plurality of soft members and that supports the plurality of shape memory material and the plurality of soft members.

9. The variable stiffness apparatus according to claim 1, wherein the first elongated member includes a cylindrical outer support member that is arranged inside the at least one high bending stiffness portion and the at least one low bending stiffness portion and that supports the at least one high bending stiffness portion and the at least one low bending stiffness portion.

10. The variable stiffness apparatus according to claim 9, wherein the outer support member includes a coil member with a bending stiffness lower than that of the at least one high bending stiffness portion.

11. The variable stiffness apparatus according to claim 9, wherein the first elongated member includes at least one heat insulating member arranged between the at least one high bending stiffness portion and the at least one low bending stiffness portion in the longitudinal axis direction.

12. The variable stiffness apparatus according to claim 1, wherein the first elongated member includes at least one heat insulating member arranged between the at least one high bending stiffness portion and the at least one low bending stiffness portion in the longitudinal axis direction.

13. The variable stiffness apparatus according to claim 12, wherein the at least one high bending stiffness portion comprises first and second high bending stiffness portions, and the first elongated member further includes a connecting member that is arranged on one of an outer periphery or an inner periphery of the at least one low bending stiffness portion and an adjacent portion of the first and second high bending stiffness portions to connect the first and second high bending stiffness portions.

14. The variable stiffness apparatus according to claim 13, wherein the connecting member includes a coil member with a bending stiffness lower than each of the first and second high bending stiffness portions.

15. An endoscope comprising:
the variable stiffness apparatus according to claim 1; and
the flexible member,
wherein the variable stiffness apparatus is disposed in the flexible member to provide the different levels of stiffness to the flexible member.

* * * * *